US00PP18773P2

(12) United States Plant Patent
Utecht

(10) Patent No.: US PP18,773 P2
(45) Date of Patent: Apr. 29, 2008

(54) ***PELARGONIUM* PLANT NAMED 'GRAWIT'**

(50) Latin Name: *Pelargonium×hortorum*
Varietal Denomination: Grawit

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/505,730

(22) Filed: Aug. 17, 2006

(51) Int. Cl.
*A01H 5/00* (2006.01)

(52) U.S. Cl. ..... Plt./326

(58) Field of Classification Search ..... Plt./326
See application file for complete search history.

(56) References Cited

PUBLICATIONS

Upov–Rom GTITM, Plant Variety Database, Jan. 2007, GTI Jouve Retrieval Software, citation for Pelargonium 'Gradwit' and 'Fiv 278', 2 pages.*

Flora–Nova Pflanzen GmbH [online] [retrieved on Jul. .30, 2007]. Retrieved from the Internet: <http://www.top500.de/details/475/flora–nova_pflanzen_gmbh_germany.php> 2 pages.*

* cited by examiner

*Primary Examiner*—Kent Bell
*Assistant Examiner*—June Hwu
(74) *Attorney, Agent, or Firm*—Jondle & Associates, P.C.

(57) ABSTRACT

A new cultivar of *Pelargonium* particularly characterized by having white, single-type, stellar-type flowers, floriferous with medium-sized inflorescences, fan-shaped leaves with slight zonation, a medium to tall-sized plant habit, a round, bushy and well-branched plant habit, good rain resistance, and an early and continuous flowering response, is disclosed.

1 Drawing Sheet

Genus and species: *Pelargonium×hortorum.*
Variety denomination: 'Grawit'.

BACKGROUND OF THE NEW PLANT

The present invention comprises a new and distinct cultivar of *perlargonium,* botanically known as *Pelargonium× hortorum,* and hereinafter referred to by the cultivar name 'Grawit'. The new cultivar is a product of a planned breeding program which had the objective of creating new varieties having stellar-type flowers in a variety of colors, good stability of flower color, medium-green foliage and a fairly compact and well-branched plant habit. 'Grawit' was discovered as a seeding resulting from the cross of the female parent 'K99-4006-2' (unpatented), a proprietary *pelargonium* plant having light-salmon, single-type flowers and the male parent 'K00-5693-7' (unpatented), a proprietary *pelargonium* plant with rose-red, double flowers.

The new cultivar was created in 2001 in Hillscheid, Germany and has been asexually reproduced repeatedly by vegetative cuttings in Galder, Gran Canaria, Spain, and Hillscheid, Germany over a four-year period. It has been found to retain its distinctive characteristics through successive asexual propagations. 'Grawit' reproduces true to type in successive generations of sexual reproduction.

Plant Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when growth under normal horticultural practices in Hillscheid, Germany.

1. Single, stellar-type, white flowers;
2. Floriferous with medium-sized inflorescences;

3. Fan-shaped leaves with slight zonation;
4. A medium-sized to tall growth habit;
5. A rounded and well-branched, plant habit;
6. Good rain resistance; and
7. An early flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of a 15-week-old, un-pinched plant grown from rooted cuttings, in 14-cm pots and grown under greenhouse and outdoor conditions which approximate those generally used in commercial practice.

DESCRIPTION OF THE NEW CULTIVAR

The following detailed description sets forth the distinctive characteristics of 'Grawit'. The data which define these characteristics were collected from asexual reproductions carried out in Hillscheid, Germany. The plant history was taken on 12-week old, un-pinched plants in 12-cm pots in a greenhouse during late May. Color readings were taken under natural light in late May from flowers grown in the greenhouse. Color references are primarily to the R.H.S. Colour Chart of The Royal Horticultural Society of London (R.H.S.), (2001).

DETAILED BOTANICAL DESCRIPTION

Classification:

Family.—Geraniaceae.

*Botanical—Pelargonium×hortorum.*

*Common names.*—Zonal geranium, stellar type.

Parentage:

*Female parent.*—'K99-4006-2' a proprietary *pelargonium* plant having light-salmon, single-type flowers (unpatented),

*Male parent.*—'K00-5693-7', a proprietary *pelargonium* plant having red-rose, double flowers (unpatented).

Plant:

*Form.*—Shrub, self-branching, mounding.

*Branching habit.*—6 to 8 branches per plant.

*Height (measured from base of the stem to the tips of the branches, excluding the inflorescence).*—24.3 cm.

*Width (plant diameter).*—33.3 cm.

*Time to produce a flowering plant.*—Plants had an average of 1.3 opened inflorescences about 9 weeks after planting rooted cuttings in Hillscheid, Germany.

*Outdoor plant performance.*—Plants continuously flower; 25 inflorescences (umbels) per plant in late summer.

Leaves:

*Arrangement.*—Alternate and appearing opposite at some parts of the nodes.

*Immature leaf color.*—Upper surface: RHS 137C. Lower surface: RHS 143C.

*Mature leaf color.*—Upper surface: RHS 137D (medium-green). Lower surface: RHS 137D.

*Zonation color.*—RHS 137A (deep-green).

*Zonation diameter.*—Inner diameter of ring: 4.0 cm to 4.5 cm. Band or belt of zonation: 2.0 cm to 2.5 cm.

*Size.*—Length: 5.5 cm. Width: 9.3 cm.

*Shape.*—Semi-circular or flabellate with distinct lobes.

*Apex.*—Rounded with lobes.

*Base.*—Cordate.

*Margin.*—Dentate.

*Texture.*—Upper surface is smooth, dull, and slightly velvety. Lower surface is smooth apart from the protruding veins, covered with fine pubescence.

*Petioles.*—Color: RHS 143C (light-green). Length: 4.0 cm to 5.5 cm. Diameter: 0.2 cm to 0.3 cm. Texture: Covered with short, dense pubescence.

Stems:

*Stem color.*—RHS 144C (light-yellow-green).

*Length.*—15 cm to 19 cm.

*Internode length.*—2.0 cm to 3.0 cm.

*Texture.*—Short pubescence and glandular hair.

Inflorescence bud: (just before petals unfold).

*Shape.*—Ellipticalm narrow.

*Size.*—Length: 1.4 cm. Width: 0.4 cm to 0.5 cm.

*Color of sepals: RHS* 144B (yellowish-green).

*Color of petals.*—RHS 155A or RHS 150D in parts.

Inflorescence:

*Inflorescence type.*—An umbel composed of 15 to 25 flowers.

*Average number of flowers and buds per inflorescence (during peak growing season).*—15–25 flowers with 5 buds per inflorescence.

*Umbel.*—Shape: Nearly semi-spherical. Diameter: 8.8 cm. Height (depth): 4.5 cm to 5.0 cm.

*Lastingness of umbel on the plant.*—About 14 to 16 days.

*Peduncle.*—Color: RHS 143C (light-green). Length: 23.3 cm. Diameter: 0.2 cm to 0.4 cm. Texture: With fine, relatively long and with short glandular hairs.

*Pedicel.*—Color: Mainly RHS 144B (yellowish-green), occasionally infused with RHS 179B (reddish-brown) anthocyanin near the flower end. Length: 2.9 cm, with a spur. Diameter: 0.1 cm to 0.2 cm. Texture: Covered with short glandular hair;

Corolla:

*Shape of corolla.*—Star-shaped with the upper petals narrower and longer than the lower petals.

*Form.*—Single.

*Diameter.*—4.4 cm.

*Depth.*—0.8 cm to 1.3 cm.

*Number of petals.*—5.

*Petaloids.*—None.

*Lastingness of individual flowers on plant.*—6 to 8 days at 18° C.

*Fragrance.*—Weakly aromatic due to the glandular hair on pedicels and peduncles:

Petals:

*Shape.*—Elliptical to lanceolate.

*Apex.*—Acute, broadly acute or rounded.

*Base.*—Acute or attenuate.

*Margin.*—Partly entire, lateral lobes and notches near the tip.

*Texture.*—Upper surface: Smooth, slightly glossy. Lower surface: Glaborous, smooth.

*Upper petals: Length:* 2.3 cm to 2.4 cm. Width: 0.4 cm to 0.6 cm. Color: Upper surface: Pure white, whiter than RHS 155D, occasionally with a slight RHS 56C (pink) hue in parts. Lower surface: White, whiter than RHS 155D. Markings: Absent.

*Lower petals.*—Length: 1.9 cm to 2.1 cm. Width: 0.8 cm to 0.9 cm. Color: Upper surface: White, lighter than RHS 155D, a weak RHS 56B (pink) hue may be developed at times. Lower surface: White, lighter than RHS 155D. Markings: Absent.

Sepals:

*Number.*—5.

*Color.*—RHS 143C (light-green) for both surfaces.

*Anthocyanin.*—Absent.

*Length.*—0.8 cm to 1.0 cm.

*Width: Largest upper sepal:* 0.2 cm to 0.3 cm. Other sepals: 0.1 cm to 0.2 cm.

*Shape.*—Ligulate to lanceolate.

*Apex.*—Acute.

*Base.*—Fused.

*Margin.*—Entire.

*Texture.*—Upper surface: Glabrous. Lower surface: Sparse long hairs.

Reproductive organs:

*Androecium.*—Number or anthers: 7. Filament length: 0.4 cm to 0.6 cm. Filament color: RHS 155D (white) to RHS 157A at lower part. Pollen color: RHS 30A (orange). Pollen amount: Abundant.

*Gynoecium.*—Pistil: Number: 1. Length: 0.7 cm. Stigma color: RHS 49B (pale-pink). Stigma shape: 5 to 6 lobed. Style color: RHS 49A (light-pink). Style length: 0.3 cm. Style shape: Filiform (filament-like) with the lobes of the stigma slanting upright and reflexed, Fruit and Seed Set: No seed set observed.

Disease and insect resistance: No particular resistance or susceptibility has been observed.

COMPARISON WITH PARENTAL AND COMMERCIAL CULTIVARS

'Grawit' differs from the female parent 'K99-4006-2' (unpatented) by having white flowers, while 'K99-4006-2' has light-salmon colored flowers.

'Grawit' differs from the male parent 'K00-5693-7' (unpatented) by having single-type, white flowers, while 'K00-5693-7' has double, red-rose flowers.

'Grawit' differs from the commercial variety 'Vextis Glitter' (unpatented) by having shorter peduncles and a more compact plant habit than 'Vectis Glitter'. In addition, 'Vectis Glitter' has pink and red speckles on the flowers, while 'Grawit' does not have these or any markings on the flowers.

I claim:

1. A new and distinct cultivar of *Pelargonium* plant as shown and described herein.

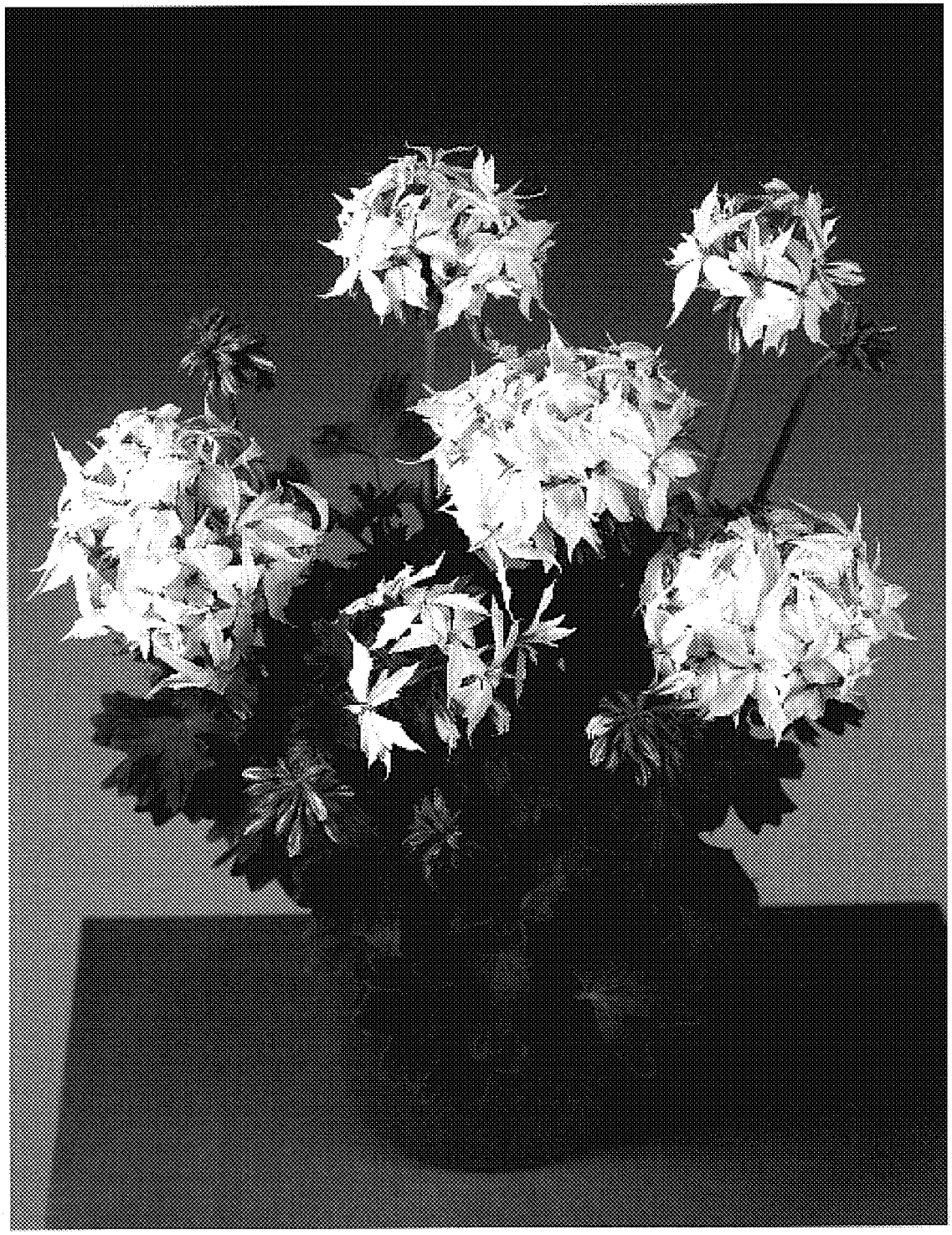

* * * * *